(12) United States Patent
Martin

(10) Patent No.: US 6,264,471 B1
(45) Date of Patent: Jul. 24, 2001

(54) LENGTH CONTROL MARKED GUTTA-PERCHA CONES AND METHOD OF INSERTION

(76) Inventor: Howard Martin, 11500 W. Hill Dr., Rockville, MD (US) 20852

( * ) Notice: Subject to any disclaimer, the term of this patent is extended or adjusted under 35 U.S.C. 154(b) by 0 days.

(21) Appl. No.: 09/265,132

(22) Filed: Mar. 8, 1999

(51) Int. Cl.[7] .................................................... A61C 5/02
(52) U.S. Cl. ........................................... 433/224; 433/81
(58) Field of Search .................................. 433/224, 102, 433/75, 81

(56) References Cited

U.S. PATENT DOCUMENTS

| | | | |
|---|---|---|---|
| 1,757,595 | * 5/1930 | Siegel | 433/224 |
| 3,772,791 | * 11/1973 | Malmin | 433/224 |
| 3,855,702 | * 12/1974 | Malmin | 433/224 |
| 5,833,457 | * 11/1998 | Johnson | 433/102 |
| 5,833,458 | * 11/1998 | Harrisson, III | 433/102 |

* cited by examiner

*Primary Examiner*—John J. Wilson
(74) *Attorney, Agent, or Firm*—Law Offices of Royal W. Craig

(57) ABSTRACT

A new and improved gutta-percha point for obturation of root canals comprising a cone with a gripping hub and an insertion tip and generally tapered toward the tip. The cone is also defined by indicia running side-to-side at predetermined positions relative to the tip to allow a visual alignment relative to a point of reference plane. The indicia further comprises a marking scale that includes a succession of discrete ring markings spaced incrementally along the gutta-percha point. A method of using the above-described gutta-percha cone is also described and this includes the steps of establishing a reference plane relative to the prepared root canal, inserting the gutta-percha cone into the prepared root canal, visually ascertaining a position of the markings relative to the reference plane to determine if the gutta-percha cone is too long, and cutting back the gutta-percha cone with reference to the markings if the gutta-percha cone is determined to be too long. The gutta-percha cone is then reset into the prepared root canal to perfect a precise and accurate fit. The new and improved obturating cone facilitates the visual ease of point of reference plane insertion into a prepared root canal for a more efficient, precise and accurate fit.

7 Claims, 1 Drawing Sheet

LENGTH CONTROL MARKED GUTTA-PERCHA CONES AND METHOD OF INSERTION

BACKGROUND OF THE INVENTION

1. Field of the Invention

The present invention relates to gutta-percha cones for obturation of root canals and, more particularly, to an improved gutta-percha cone comprising utility length control markings on the shaft of the obturating cone to facilitate the visual ease of point of reference plane insertion into a prepared root canal. The invention also comprises a method of trial cone insertion of the above-described gutta-percha cone that allows a more efficient, precise and accurate fit.

2. Description of the Background

Typical root canal procedures include accessing the root canal, preparation of the root canal and filling or obturation of the canal with a gutta-percha cone. One key step of the root canal procedure is determining the working length of the canal so that irritating chemicals and materials are kept away from the surrounding periradicular tissues. The correct working length of the root canal is important in determining success or failure because a short or a long obturation may deter healing by causing an inflammatory foreign body response or allowing an open area for fluids and bacteria to accumulate leading to future breakdown. The length of canal procedure establishes the apical extent of instrumentation as well as the ultimate apical level of the root canal filling, the gutta-percha obturator.

The requirements for a method for determining length of the canal are that it should be accurate, it should be easily and readily performed and easy to confirm. During canal preparation, the working length of the canal is determined by a combination of radiographs and electronic canal measurements. A reference point is determined for these procedures on the coronal surface of the tooth. Once this defined point is determined to be reliable and repeatable, this becomes the all important anatomic landmark that is consistently referred back to as the reference point for obturation. A gutta-percha trial cone is then inserted into the prepared root canal. Previously the gutta-percha cone is grasped between cotton pliers and is measured by a ruler to the correct length that has been predetermined. The cone is then carried into the prepared root canal until the cotton pliers touch or match up visually to the predetermined reference point or plane. If the cone lines up correctly the visual test has been passed (unless the cone is not correctly sized or the prepared canal is larger than the cone). If the cone can be pushed deeper into the canal than the length is off and the gutta-percha cone must be trimmed back so that it fits correctly. It must then be re-measured against a millimeter ruler or gauge, and replaced visually against the reference point so that it is correct. This trial and error procedure can go on and on, ultimately changing the length by several millimeters. It is very cumbersome and time consuming, and the gutta-percha cone can become contaminated during this re-calibration. Nevertheless, it is a significant and important procedure to prevent overfilling and biologic irritation to the surrounding tissue.

It would be greatly advantageous to provide a gutta-percha cone and method of use that facilitates visual point of reference plane insertion into a prepared root canal in order to accurately, easily and reliably determine the length of the canal.

SUMMARY OF THE INVENTION

It is, therefore, an object of the present invention to provide a new gutta-percha cone with utility length control markings on the shaft of the obturating cone to facilitate the visual ease of point of reference plane insertion into a prepared root canal.

It is another object t provide a method of trial point insertion using the above-described gutta-percha cone that allows a more efficient, precise and accurate fit.

In accordance with the above-described and other objects, the present invention provides a new and improved cone for obturation of root canals comprising a gutta-percha cone. The gutta-percha cone has a gripping hub and an insertion tip and is generally tapered toward the tip. The cone is also defined by indicia running side-to-side at predetermined positions relative to the tip to allow a visual alignment relative to a point of reference plane. In a prepared root canal this facilitates a precise and accurate fit of the gutta-percha cone.

The indicia is preferably a marking scale that includes a succession of discrete ring markings spaced incrementally along the gutta-percha cone.

The invention also includes the method f using the above-described gutta-percha cone, and this includes the steps of establishing a reference plane relative to the prepared root canal, inserting the gutta-percha cone into the prepared root canal, visually ascertaining a position of the markings relative to the reference plane to determine if the gutta-percha cone is too long, and cutting back the gutta-percha cone with reference to the markings if the gutta-percha cone is determined to be too long. The gutta-percha cone is then reset into the prepared root canal to perfect a precise and accurate fit.

BRIEF DESCRIPTION OF THE DRAWINGS

Other objects, features, and advantages of the present invention will become more apparent from the following detailed description of the preferred embodiment and certain modifications thereof when taken together with the accompanying drawings in which.

DETAILED DESCRIPTION OF THE PREFERRED EMBODIMENTS

Figure 1:
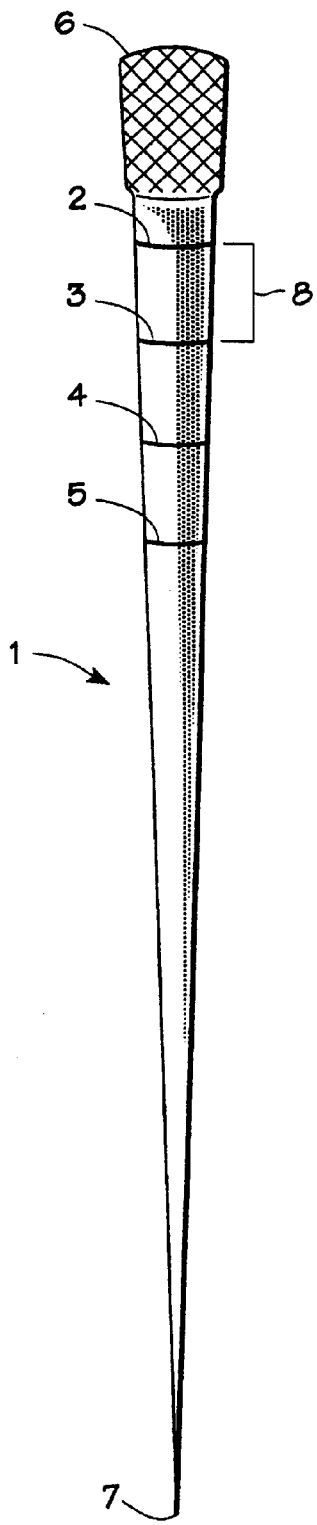
FIG. 1 is a front perspective view of a gutta-percha cone 1 with utility length control markings 2–5 in accordance with the present invention.

FIG. 1 is a front perspective view of a gutta-percha cone 1 with utility length control markings 2–6 in accordance with the present invention. As seen in FIG. 1, the gutta-percha cone 1 includes a series of utility length control markings 2–5 on the shaft of the gutta-percha obturating cone to facilitate the visual ease of point of reference plane insertion into a prepared root canal.

The markings 2–5 are positioned with respect to the tip 7 of the gutta-percha cone 1, and the preferred positions generally conform to the average length of the prepared root canal. Specifically, there are four (4) markings 2–5, and the preferred positions of the markings are at 19 mm, 21 mm, 23 mm, 25 mm (all measured from the tip 7 of the gutta-percha cone). These figures are based on the average molar root canal being about 22 mm, although it should be understood that dimensions may vary somewhat. The imprint of markings 2–5 can be accomplished by hand, stenciling, laser or any conventional permanent mechanical imprinting method, and they preferably encircle the gutta-percha cone for easy viewing directly beneath the hub 6. Hub 6 is a conventional hub such as a cross-hatched flattened-surface hub for easy gripping.

The method of application will now be described. The cone 1 is carried into the prepared root canal and is pushed into the canal starting at tip 7 until fully inserted. The dentist can visually and easily see the markings 2–5 relative to the point of reference plane. The markings 2–5 are preferably at 19 mm, 21 mm, 23 mm, 25 mm, respectively (as described above). The average molar root canal is about 22 mm. If the gutta-percha cone is too long, then the dentist can easily remove it and cut back 1 mm, 2 mm, etc., thereafter resetting the cone 1 back into the canal. If the reference plane visually falls between the existing imprinted markings the readings would be as follows: 20 mm, 22 mm, 24 mm. Therefore the total readable visual markings are actually 19 mm, 20 mm, 21 mm, 22 mm, 23 mm, 24 mm, 25 mm. These visual markings facilitate a more precise and accurate fit of the gutta-percha cone within the root canal.

These visual markings 2–5 allow a more precise and accurate fit of the gutta-percha cone 1 within the root canal. They make the trial point insertion a more efficient procedure. Moreover, the method for using the cone 1 with visual markings 2–5 is far more accurate than the conventional approach of laying the gutta-percha cone down against a millimeter ruler. The method and device are also more antiseptic as contamination can occur during the measuring phase of the old gutta-percha style cones.

In sum, these novel imprinted length control gutta-percha cones 1 according to the present invention are more accurate, easily visualized, pre-measured, and easy to confirm than regular unmarked gutta-percha cones.

Having fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims:

What is claimed is:

1. An obturator of root canals comprising a gutta-percha cone member having a gripping hub and an insertion tip and being generally tapered toward said tip, said gutta-percha cone member being defined by indicia running side-to-side at predetermined positions relative to said tip to allow a visual alignment relative to a point of reference plane, thereby facilitating a precise and accurate fit of the gutta-percha cone within a root canal.

2. The obturator of root canals according to claim 1, wherein said indicia comprise discrete markings running side-to-side at 2 mm increments relative to said tip.

3. The obturator of root canals according to claim 2, wherein said indicia comprise discrete rings around said cone member and spaced at 19 mm, 21 mm, 23 mm and 25 mm increments, respectively, relative to said tip.

4. In combination with a gutta-percha cones, a marking scale for said gutta-percha cone to allow a visual alignment relative to a point of reference plane, thereby facilitating a precise and accurate fit of the gutta-percha cone within a root canal, said marking scale comprising a succession of discrete markings spaced incrementally along said gutta-percha cone.

5. The marking scale for gutta-percha cones according to claim 4, wherein said succession of discrete markings are spaced side-to-side at 2 mm increments relative to said tip.

6. The marking scale for gutta-percha cones according to claim 5, wherein said succession of discrete 2 mm markings are spaced at 19 mm, 21 mm, 23 mm and 25 mm increments, respectively, relative to said tip.

7. A method of using a gutta-percha cone for the obturation of a root canals using a gutta-percha cone generally tapered toward an insertion tip and defined by indicia running side-to-side at predetermined positions relative to said tip to allow a visual alignment relative to a point of reference plane, the method comprising the steps of:

establishing a reference plane relative to a prepared root canal;

inserting said gutta-percha cone into said prepared root canal;

visually ascertaining a position of said markings relative to said reference plane to determine if the gutta-percha cone is too long;

cutting back said gutta-percha cone with reference to said markings of the gutta-percha cone is determined to be too long;

resetting said gutta-percha cone into said prepared root canal to perfect a precise and accurate fit.

* * * * *